United States Patent
Wisbey et al.

(10) Patent No.: US 9,526,947 B2
(45) Date of Patent: Dec. 27, 2016

(54) METHOD FOR PROVIDING A TRAINING LOAD SCHEDULE FOR PEAK PERFORMANCE POSITIONING

(71) Applicant: Logitech Europe S.A., Lausanne (CH)

(72) Inventors: Ben Wisbey, Canberra (AU); David Shepherd, Canberra (AU)

(73) Assignee: LOGITECH EUROPE, S.A., Lausanne (CH)

( * ) Notice: Subject to any disclaimer, the term of this patent is extended or adjusted under 35 U.S.C. 154(b) by 0 days.

(21) Appl. No.: 15/009,737

(22) Filed: Jan. 28, 2016

(65) Prior Publication Data

US 2016/0144237 A1    May 26, 2016

Related U.S. Application Data

(60) Division of application No. 14/142,633, filed on Dec. 27, 2013, now Pat. No. 9,314,172, which is a continuation-in-part of application No. 14/140,414, filed on Dec. 24, 2013, which is a continuation-in-part of application No. 14/137,942, filed on Dec. 20, 2013, (Continued)

(51) Int. Cl.
| | |
|---|---|
| A63B 24/00 | (2006.01) |
| G06F 19/00 | (2011.01) |
| G06K 9/00 | (2006.01) |
| A61B 5/024 | (2006.01) |
| A61B 5/11 | (2006.01) |
| A61B 5/1455 | (2006.01) |
| A61B 5/00 | (2006.01) |

(52) U.S. Cl.
CPC ....... *A63B 24/0075* (2013.01); *A61B 5/02405* (2013.01); *A61B 5/02438* (2013.01); *A61B 5/1118* (2013.01); *A61B 5/1455* (2013.01); *A61B 5/681* (2013.01); *A63B 24/0062* (2013.01); *G06F 19/3481* (2013.01); *G06K 9/00342* (2013.01)

(58) Field of Classification Search
CPC . A63B 24/00; A63B 24/0062; A63B 24/0075; G06F 19/3481; A61B 5/02405; A61B 5/02438; A61B 5/1118; A61B 5/1455; A61B 5/681; G06K 9/00342
See application file for complete search history.

(56) References Cited

U.S. PATENT DOCUMENTS 2,189,096 A    2/1940  Alonge
3,543,724 A   12/1970  Kirkpatrick et al.
(Continued)

OTHER PUBLICATIONS

"Watch Stylish Blue Light LED Round Dial Matrix Stainless from ChinaBuye.com" by YnopoB. YouTube [dated Apr. 23, 2012][online][retrieved on Dec. 31, 2015] (https://www.youtube.com/watch?v=e_LWbXHvvWg).
(Continued)

*Primary Examiner* — Glenn Richman
(74) *Attorney, Agent, or Firm* — Patterson & Sheridan LLP

(57) ABSTRACT

A system for providing a training load schedule for peak performance positioning includes an apparatus for providing a training load schedule for peak performance positioning. The apparatus includes an initial load schedule module that provides an initial load schedule. The apparatus also includes a fatigue level module that detects a fatigue level. In addition, the apparatus includes a dynamic load schedule module that creates and updates a dynamic load schedule by modifying the initial load schedule based on the fatigue level.

14 Claims, 12 Drawing Sheets

Related U.S. Application Data which is a continuation-in-part of application No. 14/137,734, filed on Dec. 20, 2013, which is a continuation-in-part of application No. 14/062,815, filed on Oct. 24, 2013.

(56) References Cited

U.S. PATENT DOCUMENTS

| | | |
|---|---|---|
| 3,978,849 A | 9/1976 | Geneen |
| 4,129,124 A | 12/1978 | Thalmann |
| 4,224,948 A | 9/1980 | Cramer et al. |
| 4,307,727 A | 12/1981 | Haynes |
| 4,331,154 A | 5/1982 | Broadwater et al. |
| 4,407,295 A | 10/1983 | Steuer et al. |
| 4,409,983 A | 10/1983 | Albert |
| 4,491,970 A | 1/1985 | LaWhite et al. |
| 5,301,154 A | 4/1994 | Suga |
| 5,392,261 A | 2/1995 | Hsu |
| 5,406,952 A | 4/1995 | Barnes et al. |
| 5,524,637 A | 6/1996 | Erickson |
| 5,734,625 A | 3/1998 | Kondo |
| 5,755,623 A | 5/1998 | Mizenko |
| 5,899,370 A | 5/1999 | Bould |
| 6,104,947 A | 8/2000 | Heikkila et al. |
| 6,151,968 A | 11/2000 | Chou |
| 6,361,503 B1 | 3/2002 | Starobin et al. |
| 6,516,222 B2 | 2/2003 | Fukuda |
| 6,554,776 B1 | 4/2003 | Snow et al. |
| 6,736,759 B1 | 5/2004 | Stubbs et al. |
| 7,192,401 B2 | 3/2007 | Saalasti et al. |
| 7,717,827 B2 | 5/2010 | Kurunmaki et al. |
| 7,914,425 B2 | 3/2011 | Hanoun |
| 8,812,428 B2 | 8/2014 | Mollicone et al. |
| 8,992,385 B2 | 3/2015 | Lemos |
| 2002/0151811 A1 | 10/2002 | Starobin et al. |
| 2002/0188210 A1 | 12/2002 | Aizawa |
| 2003/0013995 A1 | 1/2003 | Oshima et al. |
| 2003/0065269 A1 | 4/2003 | Vetter et al. |
| 2005/0056655 A1 | 3/2005 | Gary |
| 2005/0116811 A1 | 6/2005 | Eros et al. |
| 2005/0256416 A1 | 11/2005 | Chen |
| 2006/0183980 A1 | 8/2006 | Yang |
| 2007/0118043 A1 | 5/2007 | Oliver et al. |
| 2008/0132383 A1 | 6/2008 | Einav et al. |
| 2008/0228089 A1 | 9/2008 | Cho et al. |
| 2009/0312656 A1 | 12/2009 | Lau et al. |
| 2010/0197463 A1 | 8/2010 | Haughay, Jr. et al. |
| 2011/0021319 A1 | 1/2011 | Nissila et al. |
| 2011/0092790 A1 | 4/2011 | Wilder-Smith et al. |
| 2011/0190645 A1 | 8/2011 | Hunt et al. |
| 2011/0260870 A1 | 10/2011 | Bailey |
| 2012/0022341 A1 | 1/2012 | Zdeblick |
| 2012/0168471 A1 | 7/2012 | Wilson |
| 2012/0253485 A1 | 10/2012 | Weast et al. |
| 2013/0018592 A1 | 1/2013 | Mollicone et al. |
| 2013/0064049 A1 | 3/2013 | Pileri et al. |
| 2013/0237778 A1 | 9/2013 | Rouquette |
| 2014/0032234 A1 | 1/2014 | Anderson |
| 2014/0073486 A1 | 3/2014 | Ahmed et al. |
| 2014/0107493 A1 | 4/2014 | Yuen et al. |
| 2014/0228175 A1 | 8/2014 | Lemos et al. |

OTHER PUBLICATIONS

"Elite Clock Military Style LED Watch" by ledwatchsuk. YouTube [dated May 31, 2011][online][retrieved on Aug. 14, 2015].
Office Action dated Feb. 22, 2016 for U.S. Appl. No. 14/137,942.

| | | Reference Activity Instensity (RAI) | | | | | |
|---|---|---|---|---|---|---|---|
| | | RAI_0 | RAI_1 | RAI_2 | RAI_3 | RAI_4 | RAI_5 |
| Reference Activity Type (RAT) | RAT_0 | ML_0,0 | ML_0,1 | ML_0,2 | ML_0,3 | ML_0,4 | ML_0,5 |
| | RAT_1 | ML_1,0 | ML_1,1 | ML_1,2 | ML_1,3 | ML_1,4 | ML_1,5 |
| | RAT_2 | ML_2,0 | ML_2,1 | ML_2,2 | ML_2,3 | ML_2,4 | ML_2,5 |
| | RAT_3 | ML_3,0 | ML_3,1 | ML_3,2 | ML_3,3 | ML_3,4 | ML_3,5 |
| | RAT_4 | ML_4,0 | ML_4,1 | ML_4,2 | ML_4,3 | ML_4,4 | ML_4,5 |
| | RAT_5 | ML_5,0 | ML_5,1 | ML_5,2 | ML_5,3 | ML_5,4 | ML_5,5 |

Fig. 10B

| | | Frequency of Movement (F) | | | | | |
|---|---|---|---|---|---|---|---|
| | | F_0 | F_1 | F_2 | F_3 | F_4 | F_5 |
| Reference Activity Type (RAT) | RAT_0 | RAI_0,0 | RAI_0,1 | RAI_0,2 | RAI_0,3 | RAI_0,4 | RAI_0,5 |
| | RAI_2 | RAI_2,0 | RAI_2,1 | RAI_2,2 | RAI_2,3 | RAI_2,4 | RAI_2,5 |
| | RAI_3 | RAI_3,0 | RAI_3,1 | RAI_3,2 | RAI_3,3 | RAI_3,4 | RAI_3,5 |
| | RAI_4 | RAI_4,0 | RAI_4,1 | RAI_4,2 | RAI_4,3 | RAI_4,4 | RAI_4,5 |
| | RAI_5 | RAI_5,0 | RAI_5,1 | RAI_5,2 | RAI_5,3 | RAI_5,4 | RAI_5,5 |

Fig. 10C

METHOD FOR PROVIDING A TRAINING LOAD SCHEDULE FOR PEAK PERFORMANCE POSITIONING

CROSS-REFERENCE TO RELATED APPLICATIONS

This application is a divisional application of U.S. patent application Ser. No. 14/142,633, filed Dec. 27, 2013, titled "System and Method for Providing a Training Load Schedule for Peak Performance Positioning," which is a continuation-in-part of U.S. patent application Ser. No. 14/140,414, filed Dec. 24, 2013, titled "System and Method for Providing an Intelligent Goal Recommendation for Activity Level," which is a continuation-in-part of U.S. patent application Ser. No. 14/137,942, filed Dec. 20, 2013, titled "System and Method for Providing an Interpreted Recovery Score," which is a continuation-in-part of U.S. patent application Ser. No. 14/137,734, filed Dec. 20, 2013, titled "System and Method for Providing a Smart Activity Score," which is a continuation-in-part of U.S. patent application Ser. No. 14/062,815, filed Oct. 24, 2013, titled "Wristband with Removable Activity Monitoring Device." The contents of the Ser. No. 14/142,633 application, the Ser. No. 14/140,414 application, the Ser. No. 14/137,942 application, the Ser. No. 14/137,734 application, and the Ser. No. 14/062,815 application are incorporated herein by reference in their entireties.

TECHNICAL FIELD

The present disclosure relates generally to fitness monitoring devices, and more particularly to a system and method for providing a training load schedule for peak performance positioning.

DESCRIPTION OF THE RELATED ART

Previous generation fitness tracking devices generally enabled only a tracking of activity that accounts for total calories burned. Currently available fitness tracking devices now add functionality that provides universal metabolic equivalent tasks in attempt to guide a user's training schedule for an upcoming event. One issue is that currently available fitness tracking devices do not account for the performance state, or recovery state (or fatigue level), of the user in a scientific, user-specific way to provide the user with a training load schedule that will position the user in an optimal performance, or recovery zone, on the day of a scheduled, future event. Another issue is that currently available solutions do not dynamically update the training load schedule in response to measuring the user's actual fatigue (or recovery) levels on an ongoing basis.

BRIEF SUMMARY OF THE DISCLOSURE

In view of the above drawbacks, there exists a long-felt need for fitness monitoring devices that detect a fatigue level in a scientific way and provide a user-specific training load schedule that is dynamically updated based on periodic detection of the fatigue level. Further, there is a need for fitness monitoring devices that incorporate this dynamically updated load schedule to prepare a user for an event to take place on a specified date.

Embodiments of the present disclosure include systems and methods for providing a training load schedule for peak performance positioning.

One embodiment involves an apparatus for providing a training load schedule for peak performance positioning. The apparatus includes an initial load schedule module that provides an initial load schedule. The apparatus also includes a fatigue level module that detects a fatigue level. In addition, the apparatus includes a dynamic load schedule module that creates and updates a dynamic load schedule by modifying the initial load schedule based on the fatigue level. The initial load schedule and the dynamic load schedule, in one embodiment, include at least one of a recommended daily activity level and a recommended fatigue level.

The dynamic load schedule module, in one embodiment, creates and updates the dynamic load schedule when the fatigue level module detects the fatigue level. In a further embodiment, the dynamic load schedule module updates the dynamic load schedule at least once per day. In one instance, the dynamic load schedule prepares a user for an event to take place on a specified date. The dynamic load schedule module, in another instance, positions the user in an optimal performance zone on the specified date of the event.

The apparatus for providing a training load schedule, in one embodiment, also includes calendar module that maintains the dynamic load schedule and the initial load schedule. In one embodiment, the calendar module displays at least one of the dynamic load schedule and the initial load schedule using a calendar and at least one of a color-coding representation and a numerical representation. In various embodiments, at least one of the initial load schedule module, the fatigue level module, and the dynamic load schedule module is embodied in a wearable sensor.

One embodiment involves a method for providing a training load schedule for peak performance positioning. The method includes providing an initial load schedule. The method also includes detecting a fatigue level. In addition, the method includes creating and updating a dynamic load schedule by modifying the initial load schedule based on the fatigue level. The initial load schedule and the dynamic load schedule, in one embodiment, include at least one of a recommended daily activity level and a recommended fatigue level.

Creating and updating the dynamic load schedule, in one embodiment, occurs in response to detecting the fatigue level. In a further embodiment, updating the dynamic load schedule occurs at least once per day. In one instance, the dynamic load schedule prepares a user for an event to take place on a specified date. Creating and updating the dynamic load schedule, in another instance, positions the user in an optimal performance zone on the specified date of the event.

The method for providing a training load schedule, in one embodiment, also includes maintaining the initial load schedule and the dynamic load schedule in a calendar. In one illustrative case, the method includes displaying the initial load schedule and the dynamic load schedule using the calendar and at least one of a color-coding representation and a numerical representation. In a further embodiment, the method includes receiving an external dynamic load schedule and comparing the dynamic load schedule to the external dynamic load schedule.

In various embodiments, at least one of the operations of providing the initial load schedule, detecting the fatigue level, and creating and updating the dynamic load schedule by modifying the initial load schedule based on the fatigue level includes using a sensor configured to be attached to the body of a user.

One embodiment of the disclosure includes a system for providing a training load schedule for peak performance positioning. The system includes a processor and at least one computer program residing on the processor. The computer program is stored on a non-transitory computer readable medium having computer executable program code embodied thereon. The computer executable program code is configured to provide an initial load schedule. The computer executable program code is also configured to detect a fatigue level. In addition, the computer executable program code is configured to create and update a dynamic load schedule by modifying the initial load schedule based on the fatigue level.

Other features and aspects of the disclosure will become apparent from the following detailed description, taken in conjunction with the accompanying drawings, which illustrate, by way of example, the features in accordance with embodiments of the disclosure. The summary is not intended to limit the scope of the disclosure, which is defined solely by the claims attached hereto.

BRIEF DESCRIPTION OF THE DRAWINGS

The present disclosure, in accordance with one or more various embodiments, is described in detail with reference to the following figures. The figures are provided for purposes of illustration only and merely depict typical or example embodiments of the disclosure.

FIG. 10B is an example metabolic loading table

FIG. 10C is an example activity intensity library.

The figures are not intended to be exhaustive or to limit the disclosure to the precise form disclosed. It should be understood that the disclosure can be practiced with modification and alteration, and that the disclosure can be limited only by the claims and the equivalents thereof.

DETAILED DESCRIPTION

The present disclosure is directed toward systems and methods for providing a training load schedule for peak performance positioning. The disclosure is directed toward various embodiments of such systems and methods. In one such embodiment, the systems and methods are directed to a device that provides a training load schedule for peak performance positioning. According to some embodiments of the disclosure, the device may be an electronic capsule embedded in and removable from an attachable device that may be attached to a user. In one embodiment, the attachable device is a wristband. In another embodiment, the attachable device includes an activity monitoring device.

Figure 1:
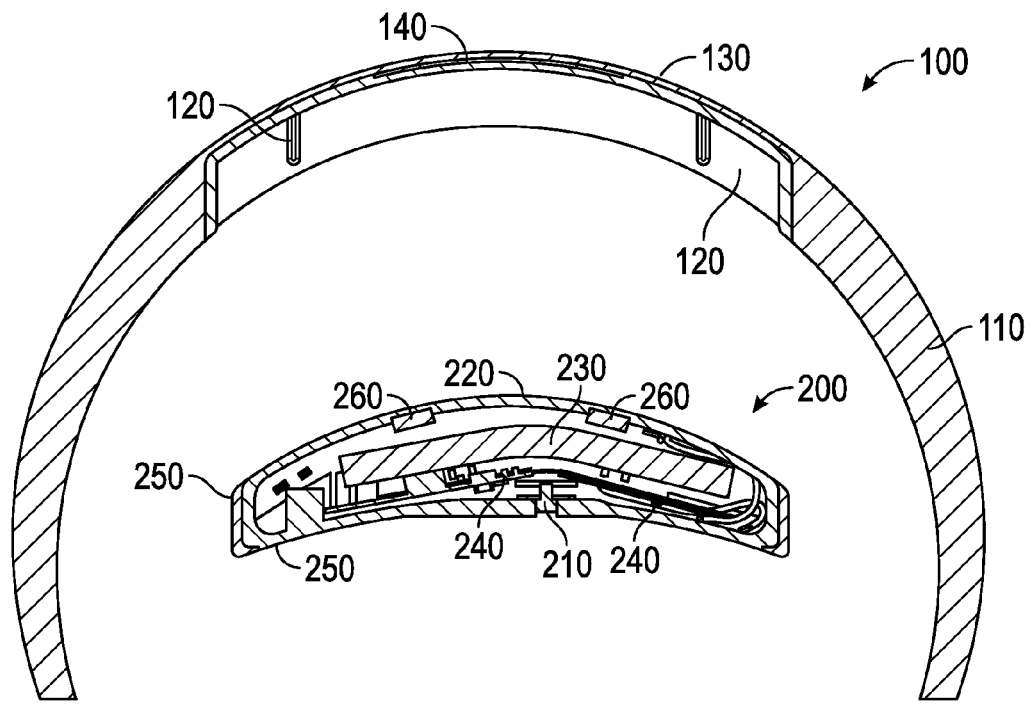
FIG. 1 illustrates a cross-sectional view of a wristband and electronic modules of an example activity monitoring device.

FIG. 1 is a diagram illustrating a cross-sectional view of an example embodiment of an activity monitoring device. Referring now to FIG. 1, an activity monitoring device comprises electronic capsule 200 and wristband 100. Electronic capsule 200 comprises wrist biosensor 210, finger biosensor 220, battery 230, one or more logic circuits 240, and casing 250.

In some embodiments, one or more logic circuits 240 comprise an accelerometer, a wireless transmitter, and circuitry. Logic circuits 240 may further comprise a gyroscope. Logic circuits 240 may be configured to process electronic input signals from biosensors 210 and 220 and from the accelerometer, store the processed signals as data, and output the data using the wireless transmitter. The transmitter is configured to communicate using available wireless communications standards. For example, in some embodiments, the wireless transmitter is a BLUETOOTH transmitter, a Wi-Fi transmitter, a GPS transmitter, a cellular transmitter, or a combination thereof. In another embodiment, the wireless transmitter further comprises a wired interface (e.g. USB, fiber optic, HDMI, etc.) for communicating stored data.

Logic circuits 240 are electrically coupled to wrist biosensor 210 and finger biosensor 220. In addition, logic circuits 240 are configured to receive and process a plurality of electric signals from each of wrist biosensor 210 and finger biosensor 220. In some embodiments, the plurality of electric signals comprise an activation time signal and a recovery time signal such that logic circuits 240 process the plurality of signals to calculate an activation recovery interval equal to the difference between the activation time signal and the recovery time signal. In some embodiments, the plurality of signals comprise electro-cardio signals from a heart, and logic circuits 240 process the electro-cardio signals to calculate and store an RR-interval, and the RR-interval is used to calculate and store a heart rate variability (HRV) value. Here, the RR-interval is equal to the delta in time between two R-waves, where the R-waves are the electro-cardio signals generated by a ventricle contraction in the heart.

In some embodiments, logic circuits 240 further detect and store metrics such as the amount of physical activity, sleep, or rest over a recent period of time, or the amount of time without physical activity over a recent period of time. Logic circuits 240 may then use the HRV, or the HRV in combination with said metrics, to calculate a fatigue level. For example, logic circuits 240 may detect the amount of physical activity and the amount of sleep a user experienced over the last 48 hours, combine those metrics with the user's HRV, and calculate a fatigue level of between 1 and 10, and the fatigue level may indicate the user's physical condition and aptitude for further physical activity that day. The fatigue level may also be calculated on a scale of between 1 and 100, or any other scale or range. The fatigue level may also be represented on a descriptive scale; for example, low, normal, and high.

In some embodiments, finger biosensor 220 and wrist biosensor 210 are replaced or supplemented by a single biosensor. In one such embodiment, the single biosensor is an optical biosensor such as a pulse oximeter configured to detect blood oxygen saturation levels. The pulse oximeter may then output a signal to logic circuits 240 indicating a detected cardiac cycle phase, and logic circuits 240 may use cardiac cycle phase data to calculate an HRV value.

Wristband 100 comprises material 110 configured to encircle a human wrist. In one embodiment, wristband 100 is adjustable. Cavity 120 is notched on the radially inward facing side of wristband 100 and shaped to substantially the same dimensions as the profile of electronic capsule 200. In addition, aperture 130 is located in material 110 within cavity 120. Aperture 130 is shaped to substantially the same dimensions as the profile of finger biosensor 220. The combination of cavity 120 and aperture 130 is designed to detachably couple to electric capsule 200 such that, when electric capsule 200 is positioned inside cavity 120, finger biosensor 220 protrudes through aperture 130. Electronic capsule 200 may further comprise one or more magnets 260 configured to secure electronic capsule 200 to cavity 120. Magnets 260 may be concealed in casing 250. Cavity 120 may be configured to conceal magnets 260 when electronic capsule 200 detachably couples to the combination of cavity 120 and aperture 130.

Wristband 100 may further comprise steel strip 140 concealed in material 110 within cavity 120. In this embodiment, when electronic capsule 200 is positioned within cavity 120, one or more magnets 260 are attracted to steel strip 140 and pull electronic capsule 200 radially outward with respect to wristband 100. The force provided by magnets 260 may detachably secure electronic capsule 200 inside cavity 120. In further embodiments, electronic capsule 200 is positioned inside cavity 120 and affixed using a form-fit, press-fit, snap-fit, friction-fit, VELCRO, or other temporary adhesion or attachment technology.

Figure 2:
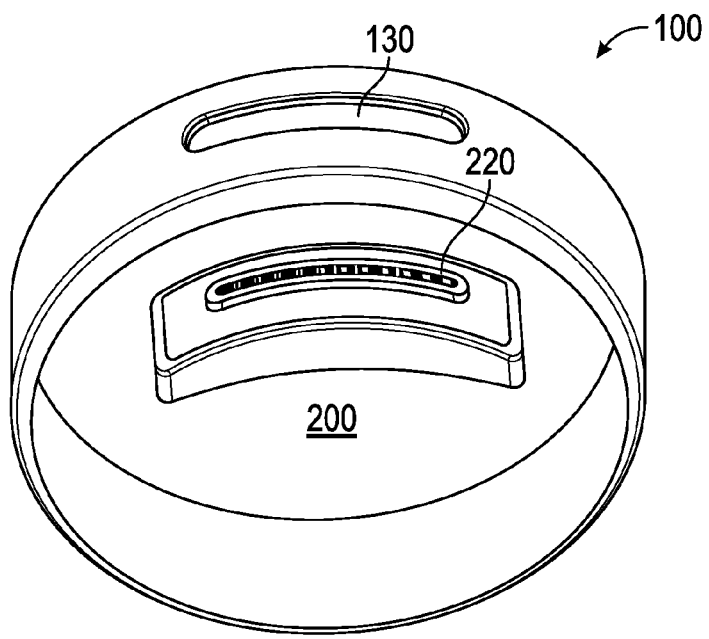
FIG. 2 illustrates a perspective view of an example activity monitoring device.
Figure 3:
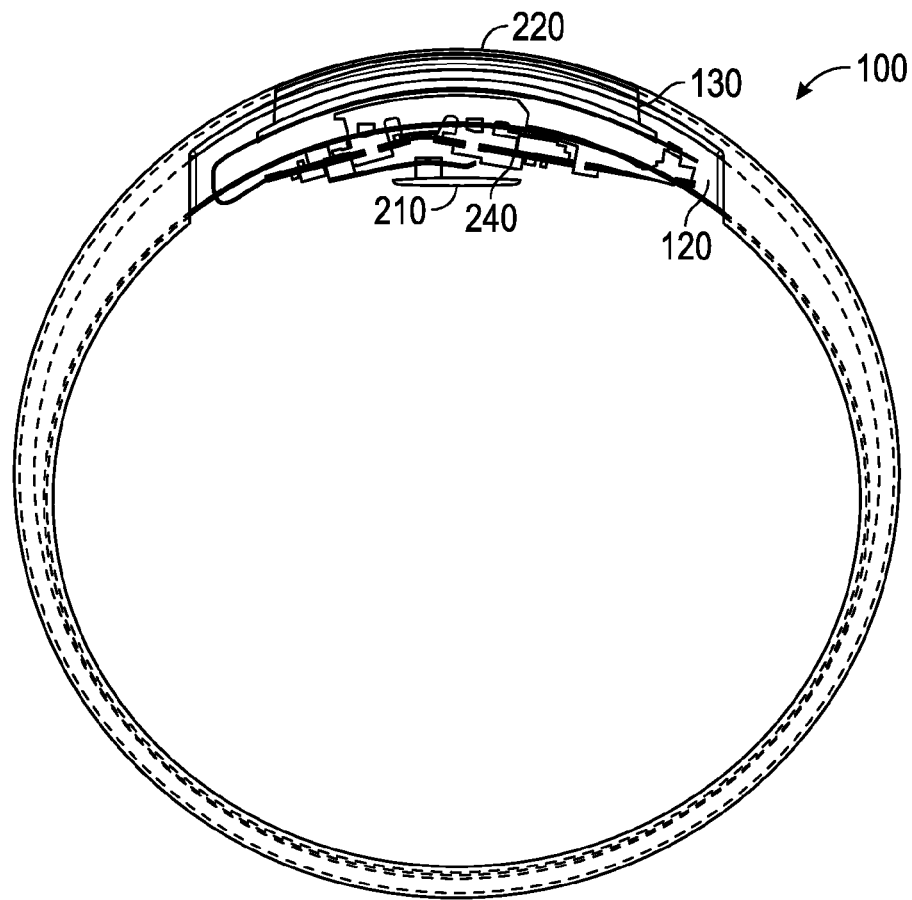
FIG. 3 illustrates a cross-sectional view of an example assembled activity monitoring device.
Figure 4:
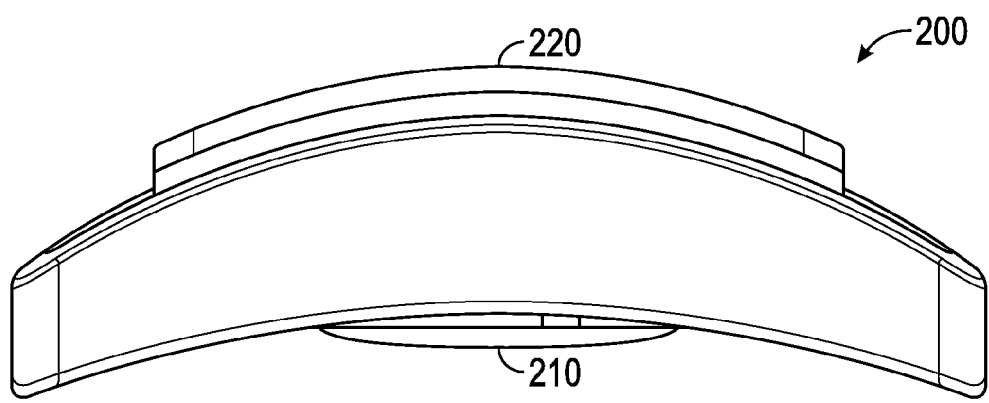
FIG. 4 illustrates a side view of an example electronic capsule.
Figure 5:
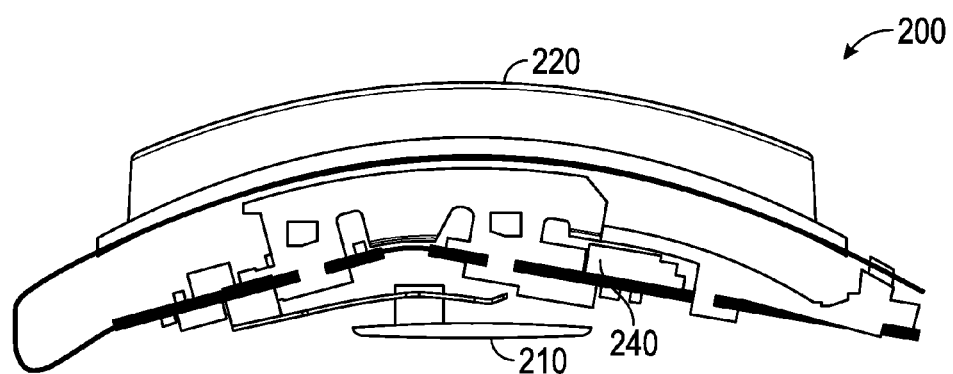
FIG. 5 illustrates a cross-sectional view of an example electronic capsule.
Figure 6:
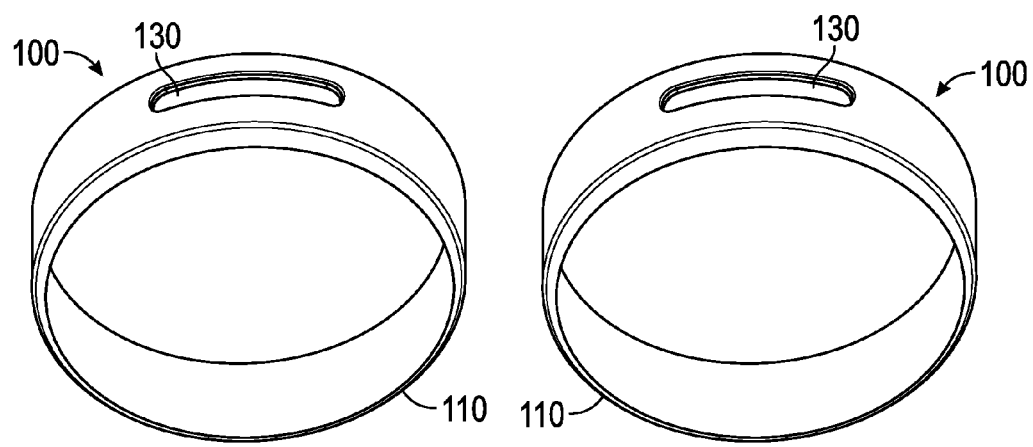
FIG. 6 illustrates perspective views of wristbands as used in one embodiment of the disclosed activity monitoring device.

FIG. 2 illustrates a perspective view of one embodiment of the disclosed activity monitoring device, in which wristband 100 and electronic capsule 200 are unassembled. FIG. 3 illustrates a cross-sectional view of one embodiment of a fully assembled wristband 100 with removable athletic monitoring device. FIG. 4 illustrates a side view of electronic capsule 200 according to one embodiment of the disclosure. FIG. 5 illustrates a cross-sectional view of electronic capsule 200. FIG. 6 is a perspective view of two possible variants of wristband 100 according to some embodiments of the disclosure. Wristbands 100 may be constructed with different dimensions, including different diameters, widths, and thicknesses, in order to accommodate different human wrist sizes and different preferences.

In some embodiments of the disclosure, electronic capsule 200 is detachably coupled to a cavity on a shoe and/or a sock. In other embodiments, electronic capsule 200 is detachably coupled to sports equipment. For example, electronic capsule 200 may be detachably coupled to a skateboard, a bicycle, a helmet, a surfboard, a paddle boat, a body board, a hang glider, or other piece of sports equipment. In these embodiments, electronic capsule 200 is affixed to the sports equipment using magnets. In other embodiments, electronic capsule 200 is affixed using a form-fit, snap-fit, press-fit, friction-fit suction cup, VELCRO, or other technology that would be apparent to one of ordinary skill in the art.

In one embodiment of the disclosure, electronic capsule 200 includes an optical sensor such as a heart rate sensor or oximeter. In this embodiment, the optical sensor is positioned to face radially inward towards a human wrist when wristband 100 is fit on the human wrist. The optical sensor, in another example, is separate from electronic capsule 200, but still detachably coupled to wristband 100 and electronically coupled to the circuit boards enclosed in electronic capsule 200. Wristband 100 and electronic capsule 200 may operate in conjunction with a system for providing a training load schedule for peak performance positioning.

Figure 7:
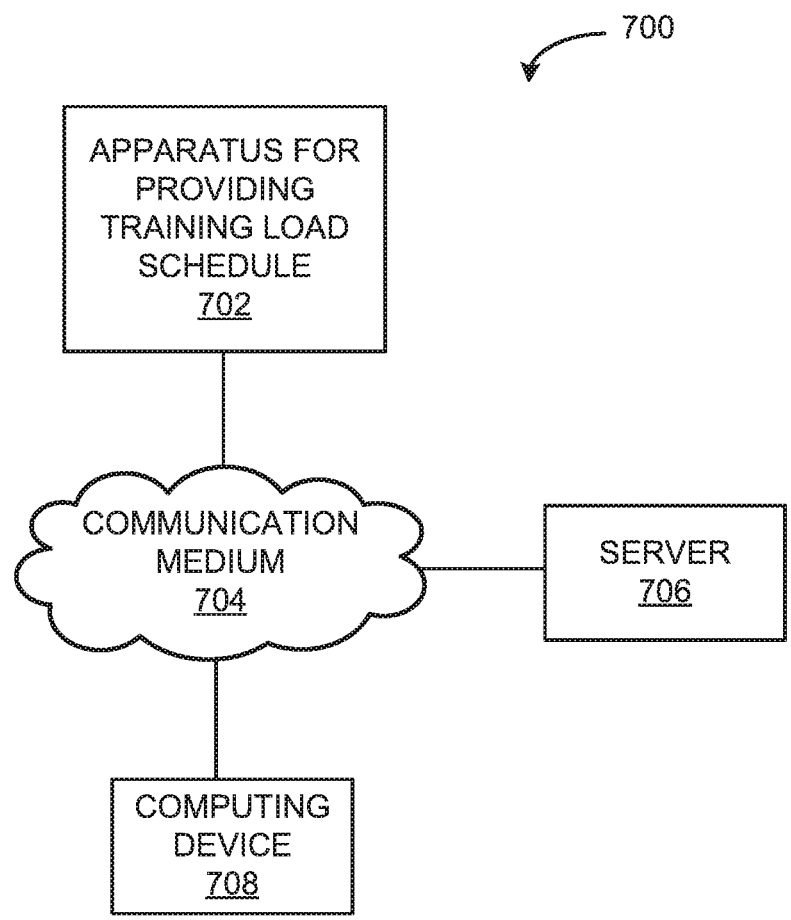
FIG. 7 illustrates an example system for providing a training load schedule.

FIG. 7 is a schematic block diagram illustrating an example system 700 for providing a training load schedule for peak performance positioning. System 700 includes apparatus for providing a training load schedule for peak performance positioning 702, communication medium 704, server 706, and computing device 708.

Communication medium 704 may be implemented in a variety of forms. For example, communication medium 704 may be an Internet connection, such as a local area network ("LAN"), a wide area network ("WAN"), a fiber optic network, internet over power lines, a hard-wired connection (e.g., a bus), and the like, or any other kind of network connection. Communication medium 704 may be implemented using any combination of routers, cables, modems, switches, fiber optics, wires, radio, and the like. Communication medium 704 may be implemented using various wireless standards, such as Bluetooth, Wi-Fi, 4G LTE, etc. One of skill in the art will recognize other ways to implement communication medium 704 for communications purposes.

Server 706 directs communications made over communication medium 704. Server 706 may be, for example, an Internet server, a router, a desktop or laptop computer, a smartphone, a tablet, a processor, a module, or the like. In one embodiment, server 706 directs communications between communication medium 704 and computing device 708. For example, server 706 may update information stored on computing device 708, or server 706 may send information to computing device 708 in real time.

Computing device 708 may take a variety of forms, such as a desktop or laptop computer, a smartphone, a tablet, a processor, a module, or the like. In addition, computing device 708 may be a processor or module embedded in a wearable sensor, a bracelets, a smart-watch, a piece of clothing, an accessory, and so on. For example, computing device 708 may be substantially similar to devices embedded in electronic capsule 200, which may be embedded in and removable from wristband 100, as illustrated in FIG. 1. Computing device 708 may communicate with other devices over communication medium 704 with or without the use of server 706. In one embodiment, computing device 708 includes apparatus 702. In various embodiments, apparatus 702 may be used to perform various processes described herein.

Figure 8:
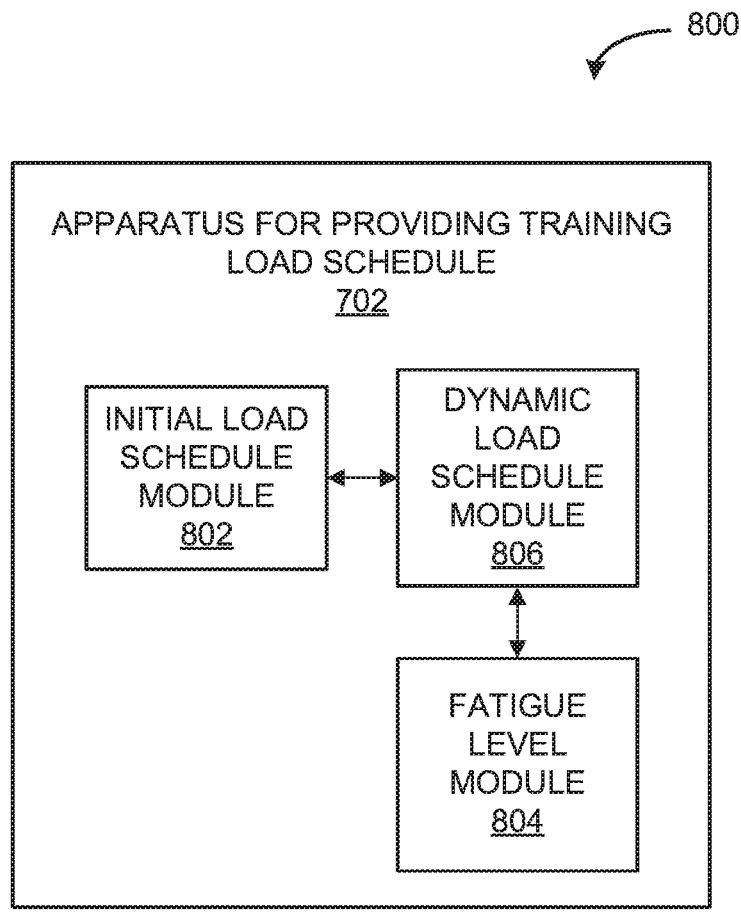
FIG. 8 illustrates an example apparatus for providing a training load schedule.

FIG. 8 is a schematic block diagram illustrating one embodiment of an apparatus for providing a training load schedule for peak performance positioning 800. Apparatus 800 includes apparatus 702 with initial load schedule module 802, fatigue level module 804, and dynamic load schedule module 806. In addition, a movement monitoring module (not shown) may monitor a movement to create a metabolic activity score based on the movement and user information. The movement monitoring module will be described below in further detail with regard to various processes.

Initial load schedule module 802 provides an initial load schedule. Initial load schedule module 802 will be described below in further detail with regard to various processes.

Fatigue level module 804 detects a fatigue level. Fatigue level module 804 will be described below in further detail with regard to various processes.

Dynamic load schedule module 806 creates and updates a dynamic load schedule by modifying the initial load schedule based on the fatigue level. Dynamic load schedule module 806 will be described below in further detail with regard to various processes.

Figure 9:
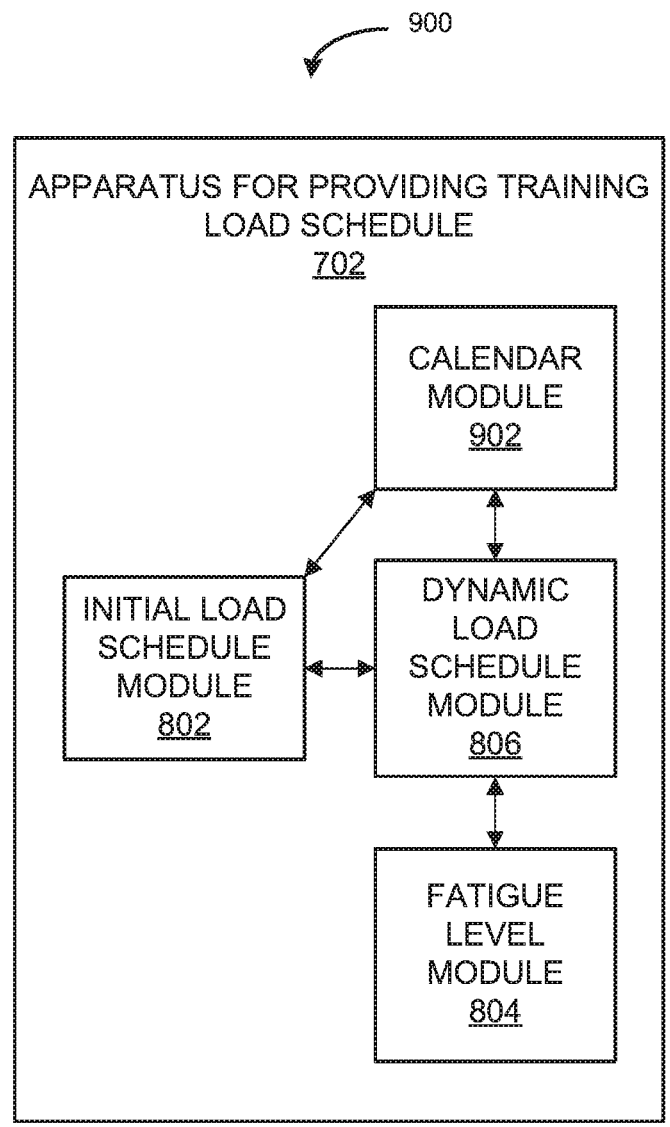
FIG. 9 illustrates another example apparatus for providing a training load schedule.

FIG. 9 is a schematic block diagram illustrating one embodiment of apparatus for providing a training load schedule for peak performance positioning 900. Apparatus 900 includes apparatus 702 with initial load schedule module 802, fatigue level module 804, and dynamic load schedule module 806. Apparatus 900 also includes calendar module 902. In one embodiment, calendar module 902 maintains the dynamic load schedule and the initial load schedule. In a further embodiment, calendar module 902 displays at least one of the dynamic load schedule and the initial load schedule using a calendar and at least one of a color-coding representation and a numerical representation. Calendar module 902 will be described below in further detail with regard to various processes.

In one embodiment, at least one of initial load schedule module 802, fatigue level module 804, dynamic load schedule module 806, and calendar module 902 is embodied in a wearable sensor, such as electronic capsule 200. In various embodiments, any of the modules described herein are embodied in electronic capsule 200 and connect to other modules described herein via communication medium 704.

Figure 10A:
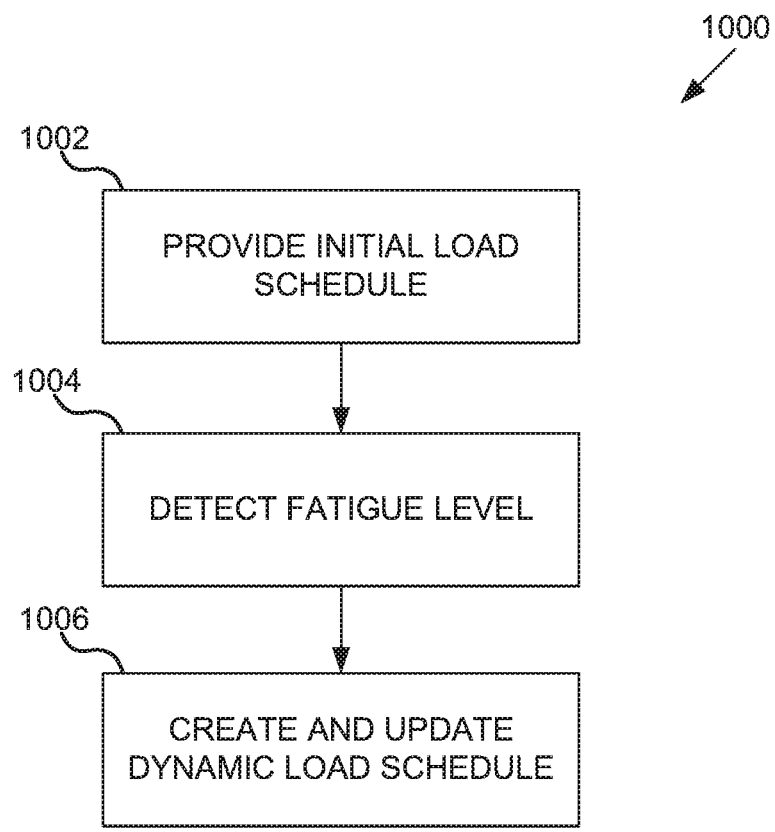
FIG. 10A is an operational flow diagram illustrating an example method for providing a training load schedule.

FIG. 10A is an operational flow diagram illustrating example method 1000 for providing a training load schedule for peak performance positioning in accordance with an embodiment of the present disclosure. The operations of method 1000 create a dynamic load schedule based on detected fatigue level. This aids in preparing a user for a future event and in positioning the user in a peak performance zone based on the user's recovery and fatigue levels. In one embodiment, apparatus 702, wristband 100, and electronic capsule 200 perform various operations of method 1000.

At operation 1002, method 1000 involves providing an initial load schedule. The initial load schedule may take various forms. For example, the initial load schedule may include a target activity level for a user to achieve for a particular period of time (e.g., day, week, month). The initial load schedule may be uniform—i.e., constant over time periods—or may vary over time periods. In one embodiment, the initial load schedule includes a recommended daily activity level as tracked by a metabolic activity score, described in detail below. For example, the initial load schedule may include a recommended daily metabolic activity score of 2,000 points per day. In another embodiment, the initial load schedule includes a recommended fatigue level. The recommended fatigue level may be a fatigue level that a user attempts to achieve as a result of the user's activities. For example, the recommended fatigue level may be 60 points each day. In both of these embodiments, the initial load schedule is a metric to which a user may conform or attempt to conform.

In one embodiment, the initial load schedule is provided based on normative data collected from a group of users. The normative data may provide a baseline initial load schedule that is not specific to the user. By way of example, the normative data may be based on publicly available data, or otherwise aggregated empirical data, related to training schedules for various evens. One example of such normative data may include a popular training regimen for a marathon, broken down into training regimens, for beginning, average, and expert runners. One of skill in the art will appreciate the many variations possible with respect the normative data that may be used to provide the initial load schedule.

In another embodiment, the initial load schedule is provided after detecting the user's fatigue level at least one time and using that fatigue level, in combination with the normative data, as a baseline for the initial load schedule. The initial load schedule, in one embodiment, is provided to prepare the user for an event to take place at a specified date. For example, the initial load schedule, if followed by the user, may prepare a user to run a marathon that is six months in the future, and so on. The initial load schedule module provides the initial load schedule, in one embodiment, by determining the fitness level required for the event, creating a rough estimate of the user's current fitness level, and determining the amount of time until the event will take place. Based on the parameters, the initial load schedule can determine a baseline training schedule for the user.

In one embodiment of method 1000, movement is monitored to create a metabolic activity score based on the movement and user information. The metabolic activity score, in one embodiment, is created from a set of metabolic loadings. The metabolic loadings may be determined by identifying a user activity type from a set of reference activity types and by identifying a user activity intensity from a set of reference activity intensities. In addition, the metabolic loadings may be determined based on information provided by a user (user information).

User information may include, for example, an individual's height, weight, age, gender, and geographic and environmental conditions. The user may provide the user information by, for example, a user interface of computing device 708, or of electronic capsule 200. User information may be determined based on various measurements—for example, measurements of the user's body-fat content or body type. Alternatively, for example, the user information may be determined by an altimeter or GPS, which may be used to determine the user's elevation, weather conditions in the user's environment, etc. In one embodiment, apparatus 702 may obtain user information from the user indirectly. For example, apparatus 702 may collect the user information from a social media account, from a digital profile, or the like.

The user information, in one embodiment, includes a user lifestyle selected from a set of reference lifestyles. For example, apparatus 702 may prompt the user for information about the user's lifestyle (e.g., via a user interface). Apparatus 702 may prompt the user to determine how active the user's lifestyle is. Additionally, the user may be prompted to select a user lifestyle from a set of reference lifestyles. The reference lifestyles may include a range of lifestyles, for example, ranging from inactive, on one end, to highly active on the other end. In such a case, the reference lifestyles that the user selects from may include sedentary, mildly active, moderately active, and heavily active.

In one instance, the user lifestyle is determined from the user as an initial matter. For example, upon initiation, apparatus 702 may prompt the user to provide a user lifestyle. In a further embodiment, the user is prompted periodically to select a user lifestyle. In this fashion, the user lifestyle selected may be aligned with the user's actual activity level as the user's activity level varies over time. In another embodiment, the user lifestyle is updated without intervention from the user.

The metabolic loadings, in one embodiment, are numerical values and may represent a rate of calories burned per unit weight per unit time (e.g., having units of kcal per kilogram per hour). By way of example, the metabolic loadings may be represented in units of oxygen uptake (e.g., in milliliters per kilogram per minute). The metabolic loadings may also represent a ratio of the metabolic rate during activity (e.g., the metabolic rate associated with a particular activity type and/or an activity intensity) to the metabolic rate during rest. The metabolic loadings, may, for example be represented in a metabolic table, such as metabolic table 1050, illustrated in FIG. 10B. In one embodiment, the metabolic loadings are specific to the user information. For example, a metabolic loading may increase for a heavier user, or for an increased elevation, but may decrease for a lighter user or for a decreased elevation.

In one embodiment, the set of metabolic loadings are determined based on the user lifestyle, in addition to the other user information. For example, the metabolic loadings for a user with a heavily active lifestyle may differ from the metabolic loadings for a user with a sedentary lifestyle. In this fashion, there may be a greater coupling between the metabolic loadings and the user's characteristics.

In various embodiments, a device (e.g., computing device 708) or a module (e.g., electronic capsule 200 or a module therein) stores or provides the metabolic loadings. The metabolic loadings may be maintained or provided by server 706 or over communication medium 704. In one embodiment, a system administrator provides the metabolic loadings based on a survey, publicly available data, scientifically determined data, compiled user data, or any other source of data. In some instances, a movement monitoring module performs the above-described operations. In various embodiments, the movement monitoring module includes a metabolic loading module and a metabolic table module that determine the metabolic loading associated with the movement.

In one embodiment, a metabolic table is maintained based on the user information. The metabolic loadings in the metabolic table may be based on the user information. In some cases, the metabolic table is maintained based on a set of standard user information, in place of or in addition to user information from the user. The standard user information may comprise, for example, the average fitness characteristics of all individuals being the same age as the user, the same height as the user, etc. In another embodiment, instead of maintaining the metabolic table based on standard information, if the user has not provided user information, maintaining the metabolic table is delayed until the user information is obtained.

As illustrated in FIG. 10B, in one embodiment, the metabolic table is maintained as metabolic table 1050. Metabolic table 1050 may be stored in computing device 708 or apparatus 702, and may include information such as reference activity types (RATs) 1054, reference activity intensities (RAIs) 1052, and/or metabolic loadings (MLs) 1060. As illustrated in FIG. 10B, in one embodiment, RATs 1054 are arranged as rows 1058 in metabolic table 1050. Each of a set of rows 1058 corresponds to different RATs 1054, and each row 1058 is designated by a row index number. For example, the first RAT row 1058 may be indexed as RAT_0, the second as RAT_1, and so on for as many rows as metabolic table 1050 may include.

The reference activity types may include typical activities, such as running, walking, sleeping, swimming, bicycling, skiing, surfing, resting, working, and so on. The reference activity types may also include a catch-all category, for example, general exercise. The reference activity types may also include atypical activities, such as skydiving, SCUBA diving, and gymnastics. In one embodiment, a user defines a user-defined activity by programming computing device 708 (e.g., by an interface on electronic capsule 200) with information about the user-defined activity, such as pattern of movement, frequency of pattern, and intensity of movement. The typical reference activities may be provided, for example, by metabolic table 1050.

In one embodiment, reference activity intensities 1052 are arranged as columns in metabolic table 1050, and metabolic table 1050 includes columns 1056, each corresponding to different RAIs 1052. Each column 1056 is designated by a different column index number. For example, the first RAI column 1056 is indexed as RAI_0, the second as RAI_1, and so on for as many columns as metabolic table 1050 may include.

The reference activity intensities include, in one embodiment, a numeric scale. For example, the reference activity intensities may include numbers ranging from one to ten (representing increasing activity intensity). The reference activities may also be represented as a range of letters, colors, and the like. The reference activity intensities may be associated with the vigorousness of an activity. For example, the reference activity intensities may represented by ranges of heart rates or breathing rates.

In one embodiment, metabolic table 1050 includes metabolic loadings 1060. Each metabolic loading 1060 corresponds to a reference activity type 1058 of the reference activity types 1054 and a reference activity intensity 1056 of the reference activity intensities 1052. Each metabolic loading 1060 corresponds to a unique combination of reference activity type 1054 and reference activity intensity 1052. For example, in the column and row arrangement discussed above, one of the reference activity types 1054 of a series of rows 1058 of reference activity types, and one of the reference activity intensities 1052 of a series of columns 1056 of reference activity intensities correspond to a particular metabolic loading 1060. In such an arrangement, each metabolic loading 1060 may be identifiable by only one combination of reference activity type 1058 and reference activity intensity 1056.

This concept is illustrated in FIG. 10B. As shown, each metabolic loading 1060 is designated using a two-dimensional index, with the first index dimension corresponding to the row 1058 number and the second index dimension corresponding to the column 1056 number of the metabolic loading 1060. For example, in FIG. 10B, ML_2,3 has a first dimension index of 2 and a second dimension index of 3. ML_2,3 corresponds to the row 1058 for RAT_2 and the column 1056 for RAI_3. Any combination of RAT_M and RAI_N may identify a corresponding ML_M,N in metabolic table 1050, where M is any number corresponding to a row 1058 number in metabolic table 1050 and N is any number corresponding to a column 1056 number in metabolic table 1050. By way of example, the reference activity type RAT_3 may be "surfing," and the reference activity intensity RAI_3 may be "4." This combination in the metabolic table 1050 corresponds to metabolic loading 1060 ML_3,3, which may, for example, represent 5.0 kcal/kg/hour (a typical value for surfing). In various embodiments, some of the above-described operations are performed by movement monitoring module 802 and some of the operations are performed by a metabolic table module.

Referring again to method 1000, in various embodiments, the movement is monitored by location tracking (e.g., Global Positioning Satellites (GPS), or a location-tracking device connected to a network via communication medium 704). The general location of the user, as well as specific movements of the user's body, are monitored. For example, the movement of the user's leg in x, y, and z directions may be monitored (e.g., by an accelerometer or gyroscope). In one embodiment, apparatus 702 receives an instruction regarding which body part is being monitored. For example, apparatus 702 may receive an instruction that the movement of a user's wrist, ankle, head, or torso is being monitored.

In various embodiments, the movement of the user is monitored and a pattern of the movement (pattern) is determined. For example, the pattern may be detected by an accelerometer or gyroscope. The pattern may be a repetition of a motion or a similar motion monitored by the method 1000; for example, the pattern may be geometric shape (e.g., a circle, line, oval) of repeated movement that is monitored. In some cases, the repetition of a motion in a geometric shape is not repeated consistently over time, but is maintained for a substantial proportion of the repetitions of movement. For instance, one occurrence of elliptical motion in a repetitive occurrence (or pattern) of ten circular motions may be monitored and determined to be a pattern of circular motion.

In further embodiments, the geometric shape of the pattern of movement is a three dimensional (3-D) shape. To illustrate, the pattern associated with the wrist of a person swimming the butterfly stroke may be monitored and analyzed into a geometric shape in three dimensions. The pattern may be complicated, but it may be described in a form can be recognized by method 1000. Such a form may include computer code that describes the spatial relationship of a set of points, along with changes in acceleration forces that are experienced along those points as, for example, a sensor travels throughout the pattern.

In various embodiments, monitoring the pattern includes monitoring the frequency with which the pattern is repeated (or pattern frequency). The pattern frequency may be derived from a repetition period of the pattern (or pattern repetition period). The pattern repetition period may be the length of time elapsing from when a device or sensor passes through a certain point in a pattern and when the device or sensor returns to that point when the pattern is repeated. For example, the sensor may be at point x, y, z at time $t\_0$. The device may then move along the trajectory of the pattern, eventually returning to point x, y, z at time $t\_1$. The pattern repetition period would be the difference between $t\_1$ and $t\_0$ (e.g., measured in seconds). The pattern frequency may be the reciprocal of the pattern repetition period, and may have units of cycles per second. When the pattern repetition period is, for example, two seconds, the pattern frequency would be 0.5 cycles per second.

In some embodiments, various other inputs may be used to determine the activity type and activity intensity. For example, monitoring the movement may include monitoring the velocity at which the user is moving (or the user velocity). The user velocity may, for example, have units of kilometers per hour. In one embodiment, the user's location information is monitored to determine user velocity. This may be done by GPS, through communication medium 704, and so on. The user velocity may be distinguished from the speed of the pattern (or pattern speed). For example, the user may be running at a user velocity of 10 km/hour, but the pattern speed of the user's wrist may be 20 km/hour at a given point (e.g., as the wrist moves from behind the user to in front of the user). The pattern speed may be monitored using, for example, an accelerometer or gyroscope.

In one embodiment, the user's altitude is monitored. This may be done, for example, using an altimeter, user location information, information entered by the user, etc. In another embodiment, the impact the user has with an object (e.g., the impact of the user's feet with ground) is monitored. This may be done using an accelerometer or gyroscope. In some cases, the ambient temperature is measured. A group of reference activity types may be associated with bands of ambient temperature. For example, when the ambient temperature is zero degrees Celsius, activities such as skiing, sledding, and ice climbing are appropriate selections for reference activity types, whereas surfing, swimming, and beach volleyball may be inappropriate. The ambient humidity may also be measured (e.g., by a hygrometer). In some cases, pattern duration (i.e., the length of time for which particular movement pattern is sustained) is measured.

Monitoring the movement, in one embodiment, is accomplished using sensors configured to be attached to a user's body. Such sensors may include a gyroscope or accelerometer to detect movement, and a heart-rate sensor, each of which may be embedded in a wristband that a user can wear on the user's wrist or ankle, such as wristband 100. Additionally, various modules and sensors that may be used to perform the above-described operations may be embedded in electronic capsule 200. In various embodiments, the above-described operations are performed by the movement monitoring module.

Method 1000, in one embodiment, involves determining the user activity type from the set of reference activity types. Once detected, the pattern may be used to determine the user activity type from a set of reference activity types. Each reference activity type is associated with a reference activity type pattern. The user activity type may be determined to be the reference activity type that has a reference activity type pattern that matches the pattern measured by method 1000.

In some cases, the pattern that matches the reference activity type pattern will not be an exact match, but will be substantially similar. In other cases, the patterns will not even be substantially similar, but it may be determined that the patterns match because they are the most similar of any patterns available. For example, the reference activity type may be determined such that the difference between the pattern of movement corresponding to this reference activity type and the pattern of movement is less than a predetermined range or ratio. In one embodiment, the pattern is looked up (for a match) in a reference activity type library. The reference activity type library may be included in the metabolic table. For example, the reference type library may include rows in a table such as the RAT rows 1058.

In further embodiments, method 1000 involves using the pattern frequency to determine the user activity type from the set of reference activity types. Several reference activity types, however, may be associated with similar patterns (e.g., because the wrist moves in a similar pattern when running versus walking). In such cases, the pattern frequency may be used to determine the activity type (e.g., because the pattern frequency for running is higher than the pattern frequency for walking).

Method 1000, in some instances, involves using additional information to determine the activity type of the user. For example, the pattern for walking may be similar to the pattern for running. The reference activity of running may be associated with higher user velocities and the reference activity of walking with lower user velocities. In this way, the velocity measured may be used to distinguish two reference activity types having similar patterns.

In other embodiments, method 1000 involves monitoring the impact the user has with the ground and determining that, because the impact is larger, the activity type, for example, is running rather than walking. If there is no impact, the activity type may be determined to be cycling (or other activity where there is no impact). In some cases, the humidity is measured to determine whether the activity is a water sport (i.e., whether the activity is being performed in the water). The reference activity types may be narrowed to those that are performed in the water, from which narrowed set of reference activity types the user activity type may be determined. In other cases, the temperature measured is used to determine the activity type.

Method 1000 may entail instructing the user to confirm the user activity type. In one embodiment, a user interface is provided such that the user can confirm whether a displayed user activity type is correct, or select the user activity type from a group of activity types.

In further embodiments, a statistical likelihood for of choices for user activity type is determined. The possible user activity types are then provided to the user in such a sequence that the most likely user activity type is listed first (and then in descending order of likelihood). For example, it may be determined that, based on the pattern, the pattern frequency, the temperature, and so on, that there is an 80% chance the user activity type is running, a 15% chance the user activity type is walking, and a 5% chance the user activity is dancing. Via a user interface, a list of these possible user activities may be provided such that the user may select the activity type the user is performing. In various embodiments, some of the above-described operations are performed by a metabolic loading module.

Method 1000, in some embodiments, also includes determining the user activity intensity from a set of reference activity intensities. The user activity intensity may be determined in a variety of ways. For example, the repetition period (or pattern frequency) and user activity type (UAT) may be associated with a reference activity intensity library to determine the user activity intensity that corresponds to a reference activity intensity. FIG. 10C illustrates one embodiment whereby this aspect of method 1000 is accomplished, including reference activity intensity library 1080. Reference activity intensity library 1080 is organized by rows 1088 of reference activity types 1084 and columns 1086 of pattern frequencies 1082. In FIG. 10C, reference activity library 1080 is implemented in a table. Reference activity library 1080 may, however, be implemented other ways.

In one embodiment, it is determined that, for user activity type 1084 UAT_0 performed at pattern frequency 1082 F_0, the reference activity intensity 1090 is RAI_0,0. For example, UAT 1084 may correspond to the reference activity type for running, a pattern frequency 1082 of 0.5 cycles per second for the user activity type may be determined. Reference activity intensity library 1080 may determine, at operation 1002, that the UAT 1084 of running at a pattern frequency 1082 of 0.5 cycles per second corresponds to an RAI 1090 of five on a scale of ten. In another embodiment, the reference activity intensity 1090 is independent of the activity type. For example, the repetition period may be five seconds, and this may correspond to an intensity level of two on a scale of ten.

Reference activity intensity library 1080, in one embodiment, is included in metabolic table 1050. In some cases, the measured repetition period (or pattern frequency) does not correspond exactly to a repetition period for a reference activity intensity in metabolic table 1050. In such cases, the correspondence may be a best-match fit, or may be a fit within a tolerance. Such a tolerance may be defined by the user or by a system administrator, for example.

In various embodiments, method 1000 involves supplementing the measurement of pattern frequency to help determine the user activity intensity from the reference activity intensities. For example, if the user activity type is skiing, it may be difficult to determine the user activity intensity because the pattern frequency may be erratic or otherwise immeasurable. In such an example, the user velocity, the user's heart rate, and other indicators (e.g., breathing rate) may be monitored to determine how hard the user is working during the activity. For example, higher heart rate may indicate higher user activity intensity. In a further embodiment, the reference activity intensity is associated with a pattern speed (i.e., the speed or velocity at which the sensor is progressing through the pattern). A higher pattern speed may correspond to a higher user activity intensity.

Method 1000, in one embodiment, determines the user activity type and the user activity intensity by using sensors configured to be attached to the user's body. Such sensors may include, for example, a gyroscope or accelerometer to detect movement, and a heart-rate sensor, each of which may be embedded in a wristband that a user can wear on the user's wrist or ankle, such as wristband 100. Additionally, various sensors and modules that may be used to preform above-described operations of method 1000 may be embedded in electronic capsule 200. In various embodiments, the above-described operations are performed by the movement monitoring module.

Method 1000, in one embodiment, includes creating and updating a metabolic activity score based on the movement and the user information. Method 1000 may also include determining a metabolic loading associated with the user and the movement. In one embodiment, a duration of the activity type at a particular activity intensity (e.g., in seconds, minutes, or hours) is determined. The metabolic activity score may be created and updated by, for example, multiplying the metabolic loading by the duration of the user activity type at a particular user activity intensity. If the user activity intensity changes, the new metabolic loading (associated with the new user activity intensity) may be multiplied by the duration of the user activity type at the new user activity intensity. In one embodiment, the activity score is represented as a numerical value. By way of example, the metabolic activity score may be updated by continually supplementing the metabolic activity score as new activities are undertaken by the user. In this way, the metabolic activity score continually increases as the user participates in more and more activities.

Referring again to FIG. 10A, operation 1004 includes detecting a fatigue level. In one embodiment, the fatigue level is the fatigue level of the user. In one embodiment, the fatigue level is a function of recovery. In various embodiments, the fatigue level is described in terms of recovery. The fatigue level may be detected in various ways. In one example, the fatigue level is detected by measuring a heart rate variability (HRV) of a user using logic circuits 240 (discussed above in reference in to FIG. 1). Further, representations of fatigue level are described above (e.g., numerical, descriptive, etc.). When the HRV is more consistent (i.e., steady, consistent amount of time between heartbeats), for example, the fatigue level may be higher. In other words, the body is less fresh and is less well-rested. When HRV is more sporadic (i.e., amount of time between heartbeats varies largely), the fatigue level may be lower. In various embodiments, the fatigue level is described in terms of an HRV score.

At operation 1004, HRV may be measured in a number of ways (discussed above in reference in to FIG. 1). Measuring HRV, in one embodiment, involves the combination of wrist biosensor 210 and finger biosensor 220. Wrist biosensor 210 may measure the heartbeat in the wrist of one arm while finger sensor 220 measures the heartbeat in a finger of the hand of the other arm. This combination allows the sensors, which in one embodiment are conductive, to measure an electrical potential through the body. Information about the electrical potential provides cardiac information (e.g., HRV, fatigue level, heart rate information, and so on), and such information may be processed at operation 1004. In other embodiments, the HRV is measured using sensors that monitor other parts of the user's body, rather than the finger and wrist. For example, the sensors may monitor the ankle, leg, arm, or torso.

In one embodiment, at operation 1004, the fatigue level is detected based solely on the HRV measured. The fatigue level, however, may be based on other measurements (e.g., measurements monitored by method 1000). For example, the fatigue level may be based on the amount of sleep that is measured for the previous night, the duration and type of user activity, and the intensity of the activity determined for a previous time period (e.g., exercise activity level in the last twenty-four hours). By way of example, these factors may include stress-related activities such as work and driving in traffic, which may generally cause a user to become fatigued. In some cases, the fatigue level is detected by comparing the HRV measured to a reference HRV. This reference HRV may be based on information gathered from a large number of people from the general public. In another embodiment, the reference HRV is based on past measurements of the user's HRV.

At operation 1004, in one embodiment, the fatigue level is detected once every twenty-four hours. This provides information about the user's fatigue level each day so that the user's activity levels may be directed according to the fatigue level. In various embodiments, the fatigue level is detected more or less often. Using the fatigue level, a user may determine whether or not an activity is necessary (or desirable), the appropriate activity intensity, and the appropriate activity duration. For example, in deciding whether to go on a run, or how long to run, the user may want to use operation 1004 to assess the user's current fatigue level. Then, the user may, for example, run for a shorter time if the user is more fatigued, or for a longer time if the user is less fatigued. In some cases, it may be beneficial to detect the fatigue level in the morning, upon the user's waking up. This may provide the user a reference for how the day's activities should proceed.

Referring again to FIG. 10A, operation 1006 involves creating and updating a dynamic load schedule by modifying the initial load schedule based on the fatigue level. In one embodiment, the initial load schedule is modified based on the fatigue level to prevent the user from becoming over-fatigued or under-fatigued. If the user becomes over-fatigued, the user may be too tired and may not be able to achieve peak performance. If the user is under-fatigued, the user may be to recovered and may not be sharp enough to achieve peak performance. In other words, by avoiding under- and over-fatigue, the dynamic load schedule positions the user in an optimal performance zone. By creating the dynamic load schedule, method 1000 provides a load schedule that adapts to the user's actual fatigue level. In one embodiment, the dynamic load schedule is, in form, substantially similar to the initial load schedule. For example, the dynamic load schedule may include a recommended daily activity level—e.g., in the form of metabolic activity score. In addition, the dynamic load schedule may include a recommended fatigue level.

In one embodiment, by continually updating based on the fatigue level, the dynamic load schedule prepares a user for an event to take place on a specified date. The dynamic load schedule, in one instance, provides a recommendation for activity level to the user, for example, in the form of metabolic activity score. By following the recommendation for activity level (or recommendation for fatigue level), the user may be able to build up the endurance and strength required for the even taking place on the specified date.

In addition, being tuned to the user's fatigue level, the dynamic load schedule, in one embodiment, places the user in peak performance (or optimal performance zone) and recovery position on the date of the specified event. In other words, the user may be positioned in a recovery state—or at a fatigue level—in which the user is neither over-fatigued or under-fatigued. Peak performance (or optimal performance zone), may correspond to, for example, a fatigue level of between 40 and 60. In such an example, the dynamic load schedule would position the user at a fatigue level of between 40 and 60 on the day of the event. For some users, however, the peak performance zone may be different, and method 1000 may determine the user's specific peak performance and recovery position by tracking the user's performance over time.

In one embodiment, the initial load schedule is provided by calculating the number of days it would take for a typical user to prepare for a specified event at a future date. In such an embodiment, the user may have characteristics different from the assumed user characteristics used to create the initial load schedule. As a result, the initial load schedule may not be tailored to the user. The dynamic load schedule, being based on the user's fatigue levels, may be tailored to the user's actual, physical response from undergoing activity, including resting from the activity.

Updating the dynamic load schedule, in one embodiment, occurs in response to detecting the fatigue level. This may be done, for example, in real time following the detection of the fatigue level at operation 1004. In one instance, the user may not desire for the dynamic load schedule to be updated in response to detecting the fatigue level. For example, if the user suspects that the fatigue level detected is inaccurate—e.g., due to user error—the user may desire to keep the non-updated dynamic load schedule because the updated version would be inaccurate. In one embodiment, the dynamic load schedule is stored upon creation (or upon being updated), such that, if the dynamic load schedule is updated contrary to the user's desire, the dynamic load schedule may be restored to a past state. The dynamic load schedule, in one embodiment, is updated at least once per day following detection of the fatigue level.

Figure 11:
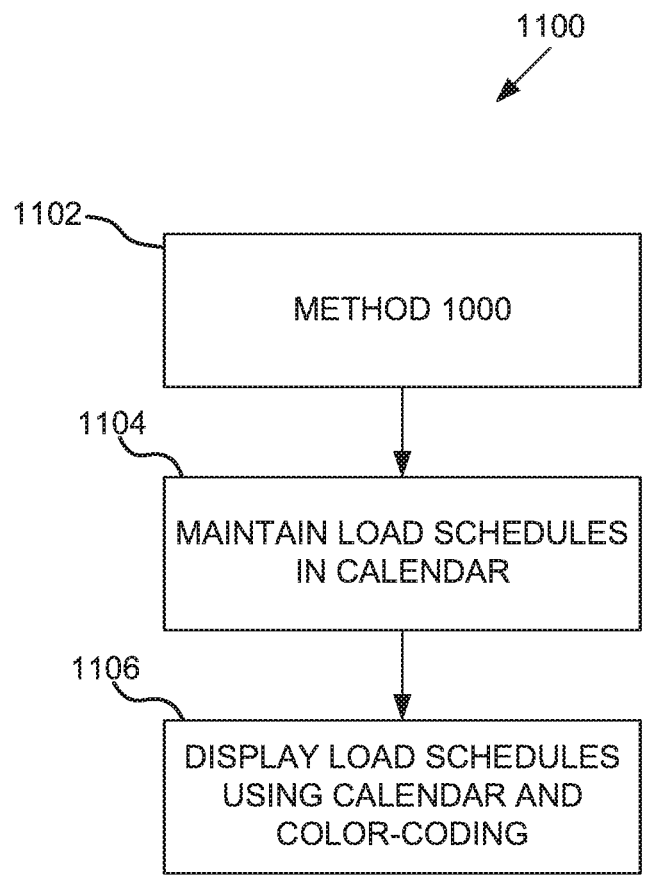
FIG. 11 is an operational flow diagram illustrating an example method for providing a training load schedule including maintaining load schedules in a calendar.

FIG. 11 is an operational flow diagram illustrating example method 1100 for providing a training load schedule for peak performance positioning. In one embodiment, apparatus 702, wristband 100, and electronic capsule 200 perform various operations of method 1100. Method 1100, in various embodiments, includes the operations of method 1000.

In one embodiment, at operation 1104, method 1100 involves maintaining the initial load schedule and the dynamic load schedule in a calendar. For example, the initial load schedule and the dynamic load schedule may be maintained as recommended activity or fatigue levels for each day represented on a week or month calendar. Other variations will be appreciated by one of ordinary skill in the art. The initial load schedule and the dynamic load schedule, in one embodiment, are maintained in the calendar with various graphical presentations. For example, the graphical presentation may include a line graph spanning multiple days that shows the recommended load schedule (initial or dynamic). In one instance of the disclosure, the dynamic load schedule is displayed overlaying the initial load schedule. This example display provides a quick comparison between the initial load schedule and the dynamic load schedule.

Referring again to FIG. 11, in one embodiment, method 1100 includes operation 1106, which involves displaying the initial load schedule and the dynamic load schedule using the calendar and at least one of a color-coding representation and a numerical representation. For example, the initial load schedule and the dynamic load schedule may be represented as a numerical value on the calendar (e.g., dynamic load schedule for Oct. 12, 2014, may be 2,000).

Moreover, the initial and dynamic load schedules may be, for example, represented using a series of colors to indicate the recommended load. In such an example, red may indicate a high recommended load (i.e., very active day), yellow may indicate a moderate load (i.e., normally active day), and green may indicate a light load (i.e., restful day). In another example, the color might indicate whether the user is on pace to be prepared for the specified event. This provides for at-a-glance, understandable information that the user can rely on to direct the user's activities. In a further embodiment, the load schedules are presented using a combination of numerical, color-coded, and graphical representations.

Figure 12:
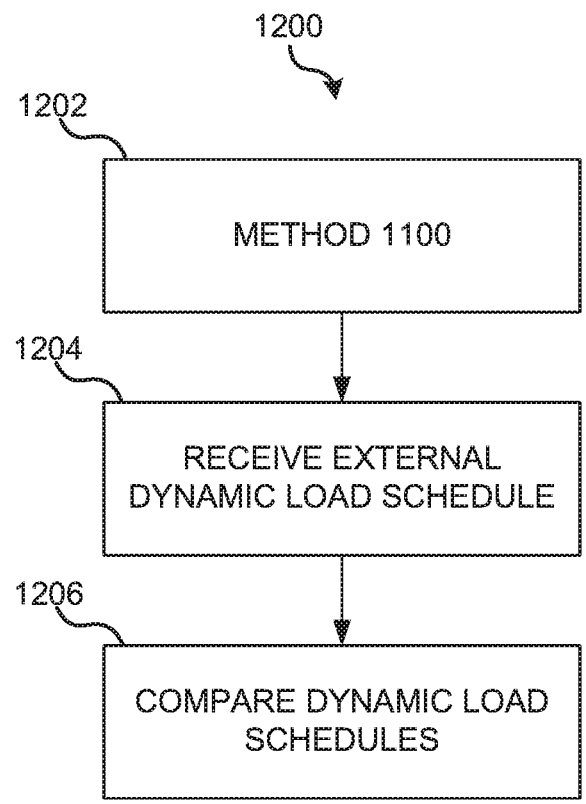
FIG. 12 is an operational flow diagram illustrating an example method for providing a training load schedule including comparing dynamic load schedules.

FIG. 12 is an operational flow diagram illustrating example method 1200 for providing a training load schedule for peak performance positioning in accordance with an embodiment of the present disclosure. In one embodiment, apparatus 702, wristband 100, and electronic capsule 200 perform various operations of method 1200. Method 1200, in various embodiments, includes the operations of method 1100.

In one embodiment, at operation 1204, method 1200 involves receiving an external dynamic load schedule. The external dynamic load schedule may be received in a number of ways (e.g., via communication medium 704). The external dynamic load schedule may be created and updated in a manner similar to the creating and updating of the dynamic load schedule (e.g., at operation 1006). The external dynamic load schedule may be from a second user, who is any user other than the user. For example, the second user may be a friend or associate of the first user.

In one instance, the external dynamic load schedule is a past dynamic load schedule of the user that is associated with a past event. For example, the external dynamic load schedule may be the user's dynamic load schedule for the 2013 Saint George Marathon. In this way, method 1200 may provide ghost-training capabilities whereby the user can train against the user's past training regimens. In various embodiments, operation 1204 is performed by dynamic load schedule module 806.

At operation 1206, an embodiment of method 1200 involves comparing the dynamic load schedule to the external dynamic load schedule. Operation 1206, in one embodiment, entails displaying a graphical, numerical, or color-coded representation of the dynamic load schedule. Method 1200 may overlay that representation with a similar representation of the external dynamic load schedule. One of ordinary skill in the art will appreciate other ways that method 1200 may compare the load schedules at operation 1206. In another embodiment, method 1200 compares the dynamic load schedule to multiple external dynamic load schedules associated with other users. Operation 1206, in a further embodiment, compares the dynamic load schedule to multiple past dynamic load schedules of the user that are associated with multiple past events. This provides a metric whereby the user can ghost train against the user's own past performance training in a set of past events that may be similar to the upcoming event.

Operation 1206, in other words, allows the user to compare the user's dynamic load schedule, which is based on the user's fatigue level and a specified event in the future, to the external dynamic load schedule of other users, which may be based on the other users' fatigue levels and future events specified by the other users. In the case that the specified event from the user and the specified even from the external users are the same event, operation 1206 provides the user with a relative metric for the user's preparation for the specified event. This may allow the user to compete against the other users as the user and the other users train or prepare for an upcoming, scheduled event. In various embodiments, operation 1206 is performed dynamic load schedule module 806.

In one embodiment, the operations of method 1000, method 1100, and method 1200 are performed using sensors configured to be attached to the body (e.g., the user's body). Such sensors may include a gyroscope or accelerometer to detect movement, and a heart-rate sensor, each of which may be embedded in a wristband that a user can wear on the user's wrist or ankle, such as wristband 100, or a device or module such as electronic capsule 200. Such sensors may be used to perform the operations of providing the initial load schedule, detecting the fatigue level, and creating and updating the dynamic load schedule, and any other operation disclosed herein.

Figure 13:
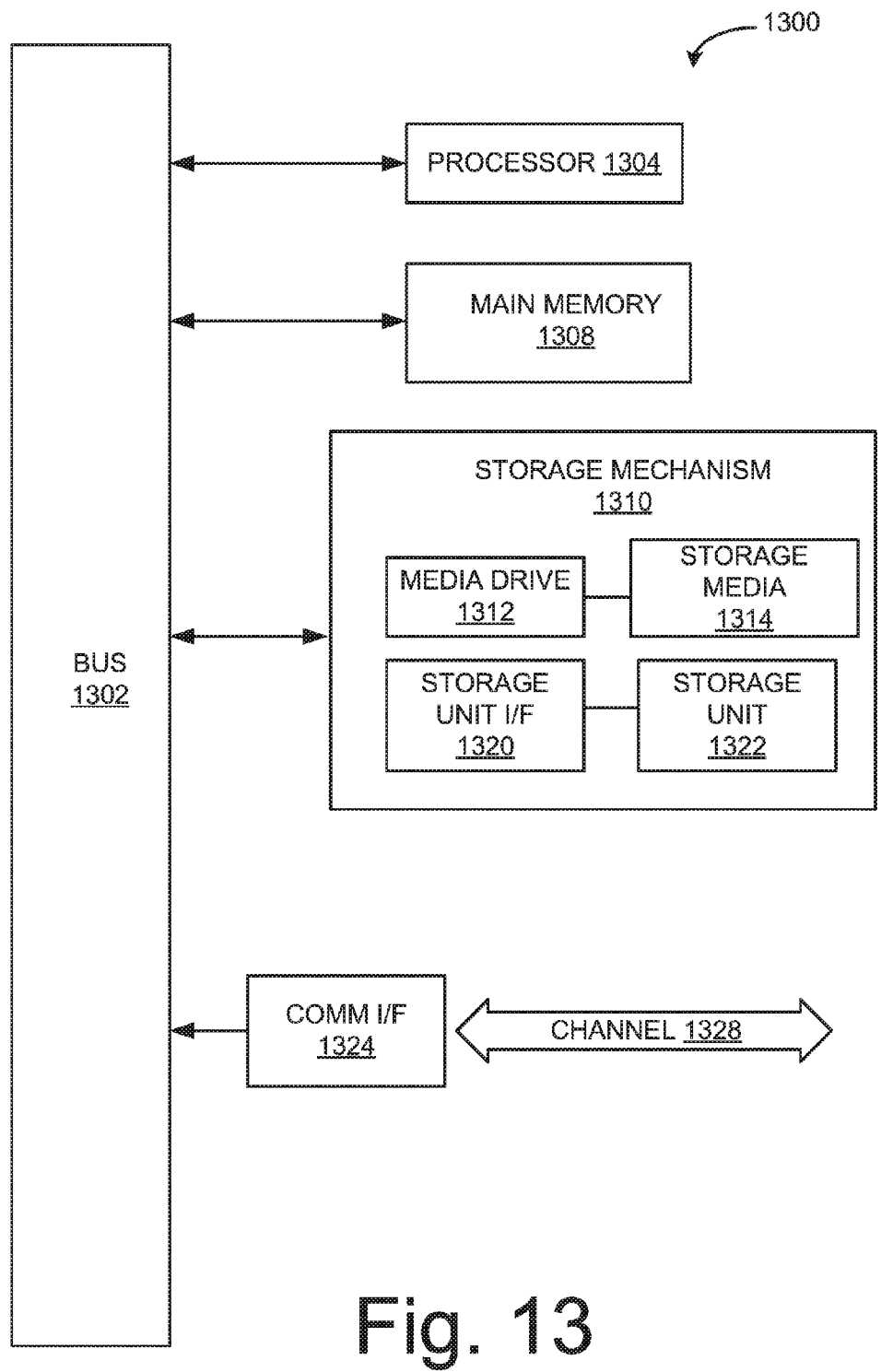
FIG. 13 illustrates an example computing module that may be used to implement various features of the systems and methods disclosed herein.

FIG. 13 illustrates an example computing module that may be used to implement various features of the systems and methods disclosed herein. In one embodiment, the computing module includes a processor and a set of computer programs residing on the processor. The set of computer programs is stored on a non-transitory computer readable medium having computer executable program code embodied thereon. The computer executable code is configured to provide an initial load schedule. The computer executable code is further configured to detect a fatigue level. The computer executable code is also configured to create and update a dynamic load schedule by modifying the initial load schedule based on the fatigue level.

The example computing module may be used to implement these various features in a variety of ways, as described above with reference to the methods illustrated in FIGS. 10A, 10B, 10C, 11, and 12, and as will be appreciated by one of ordinary skill in the art.

As used herein, the term module might describe a given unit of functionality that can be performed in accordance with one or more embodiments of the present application. As used herein, a module might be implemented utilizing any form of hardware, software, or a combination thereof. For example, one or more processors, controllers, ASICs, PLAs, PALs, CPLDs, FPGAs, logical components, software routines or other mechanisms might be implemented to make up a module. In implementation, the various modules described herein might be implemented as discrete modules or the functions and features described can be shared in part or in total among one or more modules. In other words, as would be apparent to one of ordinary skill in the art after reading this description, the various features and functionality described herein may be implemented in any given application and can be implemented in one or more separate or shared modules in various combinations and permutations. Even though various features or elements of functionality may be individually described or claimed as separate modules, one of ordinary skill in the art will understand that these features and functionality can be shared among one or more common software and hardware elements, and such description shall not require or imply that separate hardware or software components are used to implement such features or functionality.

Where components or modules of the application are implemented in whole or in part using software, in one embodiment, these software elements can be implemented to operate with a computing or processing module capable of carrying out the functionality described with respect thereto. One such example computing module is shown in FIG. 13. Various embodiments are described in terms of this example-computing module 1300. After reading this description, it will become apparent to a person skilled in the relevant art how to implement the application using other computing modules or architectures.

Referring now to FIG. 13, computing module 1300 may represent, for example, computing or processing capabilities found within desktop, laptop, notebook, and tablet computers; hand-held computing devices (tablets, PDA's, smart phones, cell phones, palmtops, smart-watches, smart-glasses etc.); mainframes, supercomputers, workstations or servers; or any other type of special-purpose or general-purpose computing devices as may be desirable or appropriate for a given application or environment. Computing module 1300 might also represent computing capabilities embedded within or otherwise available to a given device. For example, a computing module might be found in other electronic devices such as, for example, digital cameras, navigation systems, cellular telephones, portable computing devices, modems, routers, WAPs, terminals and other electronic devices that might include some form of processing capability.

Computing module 1300 might include, for example, one or more processors, controllers, control modules, or other processing devices, such as a processor 1304. Processor 1304 might be implemented using a general-purpose or special-purpose processing engine such as, for example, a microprocessor, controller, or other control logic. In the illustrated example, processor 1304 is connected to a bus 1302, although any communication medium can be used to facilitate interaction with other components of computing module 1300 or to communicate externally.

Computing module 1300 might also include one or more memory modules, simply referred to herein as main memory 1308. For example, preferably random access memory (RAM) or other dynamic memory, might be used for storing information and instructions to be executed by processor 1304. Main memory 1308 might also be used for storing temporary variables or other intermediate information during execution of instructions to be executed by processor 1304. Computing module 1300 might likewise include a read only memory ("ROM") or other static storage device coupled to bus 1302 for storing static information and instructions for processor 1304.

The computing module 1300 might also include one or more various forms of information storage mechanism 1310, which might include, for example, a media drive 1312 and a storage unit interface 1320. The media drive 1312 might include a drive or other mechanism to support fixed or removable storage media 1314. For example, a hard disk drive, a solid state drive, a magnetic tape drive, an optical disk drive, a CD or DVD drive (R or RW), or other removable or fixed media drive might be provided. Accordingly, storage media 1314 might include, for example, a hard disk, a solid state drive, magnetic tape, cartridge, optical disk, a CD or DVD, or other fixed or removable medium that is read by, written to or accessed by media drive 1312. As these examples illustrate, the storage media 1314 can include a computer usable storage medium having stored therein computer software or data.

In alternative embodiments, information storage mechanism 1310 might include other similar instrumentalities for allowing computer programs or other instructions or data to be loaded into computing module 1300. Such instrumentalities might include, for example, a fixed or removable storage unit 1322 and a storage interface 1320. Examples of such storage units 1322 and storage interfaces 1320 can include a program cartridge and cartridge interface, a removable memory (for example, a flash memory or other removable memory module) and memory slot, a PCMCIA slot and card, and other fixed or removable storage units 1322 and storage interfaces 1320 that allow software and data to be transferred from the storage unit 1322 to computing module 1300.

Computing module 1300 might also include a communications interface 1324. Communications interface 1324 might be used to allow software and data to be transferred between computing module 1300 and external devices. Examples of communications interface 1324 might include a modem or softmodem, a network interface (such as an Ethernet, network interface card, WiMedia, IEEE 802.XX or other interface), a communications port (such as for example, a USB port, IR port, RS232 port Bluetooth® interface, or other port), or other communications interface. Software and data transferred via communications interface 1324 might typically be carried on signals, which can be electronic, electromagnetic (which includes optical) or other signals capable of being exchanged by a given communications interface 1324. These signals might be provided to communications interface 1324 via a channel 1328. This channel 1328 might carry signals and might be implemented using a wired or wireless communication medium. Some examples of a channel might include a phone line, a cellular link, an RF link, an optical link, a network interface, a local or wide area network, and other wired or wireless communications channels.

In this document, the terms "computer program medium" and "computer usable medium" are used to generally refer to transitory or non-transitory media such as, for example, memory 1308, storage unit 1320, media 1314, and channel 1328. These and other various forms of computer program media or computer usable media may be involved in carrying one or more sequences of one or more instructions to a processing device for execution. Such instructions embodied on the medium are generally referred to as "computer program code" or a "computer program product" (which may be grouped in the form of computer programs or other groupings). When executed, such instructions might enable the computing module 1300 to perform features or functions of the present application as discussed herein.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed in multiple groupings or packages or across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

While various embodiments of the present disclosure have been described above, it should be understood that they have been presented by way of example only, and not of limitation. Likewise, the various diagrams may depict an example architectural or other configuration for the disclosure, which is done to aid in understanding the features and functionality that can be included in the disclosure. The disclosure is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the present disclosure. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the disclosure is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosure, whether or not such embodiments are described and whether or not such features are presented as being a part of a described embodiment. Thus, the breadth and scope of the present disclosure should not be limited by any of the above-described exemplary embodiments.

What is claimed is:

1. A method for providing a training load schedule for peak performance positioning, comprising:
providing an initial load schedule, which is stored in non-volatile memory, to a user, wherein the provided initial load schedule includes information that allows the user to obtain peak performance positioning for an event to take place on a specified date in the future;
determining a fatigue level of the user using one or more signals from one or more sensors worn by the user; and
creating and updating a dynamic load schedule stored in non-volatile memory by modifying the initial load schedule based on the determined fatigue level, wherein the dynamic load schedule includes information that allows the user to obtain the peak performance positioning for the event to take place on the specified date in the future.

2. The method of claim 1, wherein the initial load schedule and the dynamic load schedule comprise at least one of a recommended daily activity level and a recommended fatigue level.

3. The method of claim 1, wherein creating and updating the dynamic load schedule occurs in response to determining the fatigue level.

4. The method of claim 3, wherein updating the dynamic load schedule occurs at least once per day.

5. The method of claim 1, wherein creating and updating the dynamic load schedule comprises positioning the user in an optimal performance zone on the specified date of the event.

6. The method of claim 1, further comprising maintaining the initial load schedule and the dynamic load schedule in a calendar.

7. The method of claim 6, further comprising displaying the initial load schedule and the dynamic load schedule using the calendar and at least one of a color-coding representation and a numerical representation.

8. The method of claim 1, further comprising:
receiving an external dynamic load schedule; and
comparing the dynamic load schedule to the external dynamic load schedule.

9. The method of claim 1, wherein providing the initial load schedule comprises using a sensor configured to be attached to the body of the user.

10. The method of claim 1, wherein determining the fatigue level of the user comprises determining an amount of sleep by the user, an amount of physical activity by the user, and a heart rate variability (HRV) of the user over a period of time.

11. The method of claim 1, wherein the one or more sensors includes a pulse oximeter.

12. The method of claim 1, further comprising:
determining the user's initial fatigue level using the one or more sensors worn by the user and using the initial fatigue level to determine the initial load schedule.

13. The method of claim 1, wherein the initial load schedule is determined based on a fitness level required for the event, an estimate of the user's current fitness level, and an amount of time until the specified date of the event.

14. The method of claim 1, further comprising
tracking the user's performance over time;
determining a fatigue level at which the user performs best; and
updating the dynamic load schedule to position the user at the fatigue level at which the user performs best.

* * * * *